US008580512B2

(12) United States Patent
Marcus et al.

(10) Patent No.: US 8,580,512 B2
(45) Date of Patent: Nov. 12, 2013

(54) YEAST-BASED METHODS OF IDENTIFYING NUCLEIC ACIDS AND COMPOUNDS FOR TREATING NEURODEGENERATIVE DISEASES

(75) Inventors: Stevan Marcus, Tuscaloosa, AL (US); Galina Gulis, Brasilia (BR); P. Connor Johnson, Cullman, AL (US)

(73) Assignee: University of Alabama, Tuscaloosa, AL (US)

( * ) Notice: Subject to any disclaimer, the term of this patent is extended or adjusted under 35 U.S.C. 154(b) by 146 days.

(21) Appl. No.: 13/063,865

(22) PCT Filed: Nov. 20, 2009

(86) PCT No.: PCT/US2009/065308
§ 371 (c)(1),
(2), (4) Date: Mar. 14, 2011

(87) PCT Pub. No.: WO2010/074859
PCT Pub. Date: Jul. 1, 2010

(65) Prior Publication Data
US 2011/0250607 A1    Oct. 13, 2011

Related U.S. Application Data

(60) Provisional application No. 61/139,787, filed on Dec. 22, 2008.

(51) Int. Cl.
*C12Q 1/68* (2006.01)
(52) U.S. Cl.
USPC .......................................... 435/6.13; 435/29
(58) Field of Classification Search
USPC .................................................. 435/6.13, 29
See application file for complete search history.

(56) References Cited

PUBLICATIONS

Heslot et al.; Respiratory Metabolism of a "Petite Negative" Yeast *Schizosaccharomyces pombe* 972h-1; Journal of Bacteriology, vol. 104, No. 1, p. 473-481, Oct. 1970.*
Moore et al.; *Schizosaccharomyces pombe* Mitochondria: Morphological, Respiratory and Protein Import Characteristics; Yeast; vol. 8: 923-933 (1992).*

International Search Report and Written Opinion dated Jul. 7, 2010.
Mounolou, et al., "Resistance and Sensitivity to Rotenone in *Saccharomyces cerevisiae*: Possibility of a Genetic Reexamination," FEBS Lett. Feb. 1, 1973, vol. 29, No. 3, pp. 275-279.
Sherer, et al., "Mechanism of Toxicity in Rotenone Models of Parking's Disease," J. Neurosci., Nov. 26, 2003, vol. 23, No. 34, pp. 10756-10764.
Marella, et al., "Mechanism of Cell Death Caused by Complex 1 Defects in a Rat Dopaminergic Cell Line," J. Biol. Che., Aug. 17, 2007, vol. 282, No. 33, pp. 24146-24156.
Seo, et al., "Use of the NADH-quinone Oxidoreductase (NDI1) Gene of *Saccharomyces cerevisiae* as a Possible Cure for Complex I Defects in Human Cells," J. Biol. Chem. Dec. 1, 2000, vol. 275, No. 48, pp. 377774-377778.
Seo, et al., "In Vivo Complementation of Complex I by the Yeast Ndi1 Enzyme, Possible Application for Treatment of Parkinson Disease." J. Biol. Chem., May 19, 2006, vol. 281, No. 20, pp. 14250-14255.
Chiron, et al., Studying Mitochondria in an Attractive Model: *Schizosaccharomyces pombe*,: Methods Mol. Biol. 2007, vol. 372, pp. 91-105.
Luo, et al., "Phosphatidylethanolamine Is Required for Normal Cell Morphology and Cytokinesis in the Fission Yeast *Schizosaccharomyces pombe*," Eukaryotic Cell, May 2009, pp. 790-799.
Wang, et al., "The MPA Kinase Pmk1 and Protein Kinase A Are Required for Rotenone Resistance in the Fission Yeast, *Schizosaccharomyces pombe*," Biochemical abd Biophysical Research Communications 399 (2020) pp. 123-128.

* cited by examiner

*Primary Examiner* — Michele K Joike
*Assistant Examiner* — Antonio Galisteo Gonzalez
(74) *Attorney, Agent, or Firm* — Thomas Horstemeyer, LLP; Lisa C. Pavento

(57) ABSTRACT

The disclosure encompasses methods for the screening of small molecules or nucleic acids that may reverse the inhibition of growth of the unicellular yeast *Schizosaccharomyces pombe* by rotenone. The use of a yeast as the screening target allows for the high-throughput screening of small molecule and nucleic acid libraries for candidates that may then be screened in animal models as therapeutic agents for the treatment of neurodegenerative diseases. The plant-derived isoflavonoid, rotenone, while only moderately inhibitory to *S. pombe* cell growth on complex rich medium, is highly inhibitory to growth on synthetic minimal medium. *S. pombe* cells carrying a deletion in the gene pmk1 are hypersensitive to rotenone. *S. pombe*, therefore, provides a model for elucidating complex 1-independent targets of rotenone, and can serve as a screening tool for identifying compounds or oligonucleotides potentially able to reverse the effects of rotenone or Parkinson's disease in animal or human subjects.

6 Claims, 7 Drawing Sheets

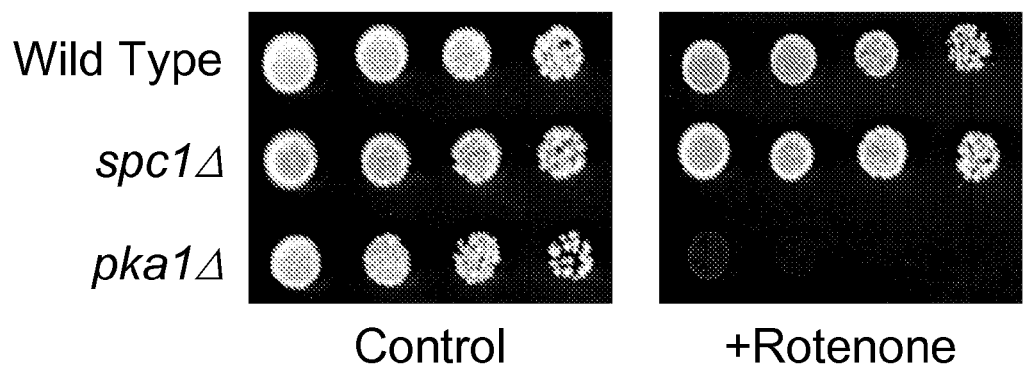
Fig. 4
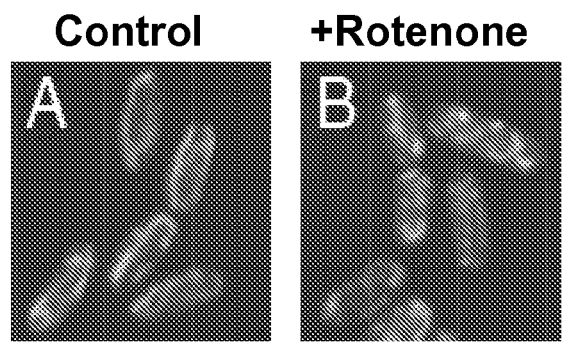
Fig. 5A   Fig. 5B
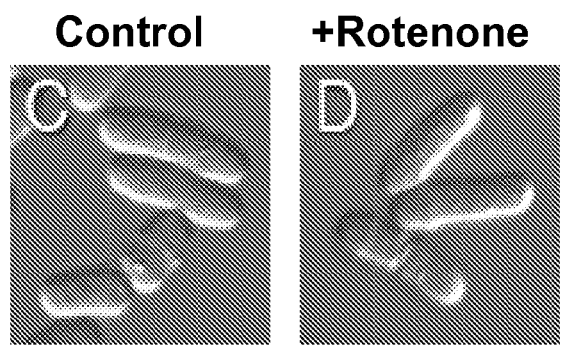
Fig. 5C   Fig. 5D

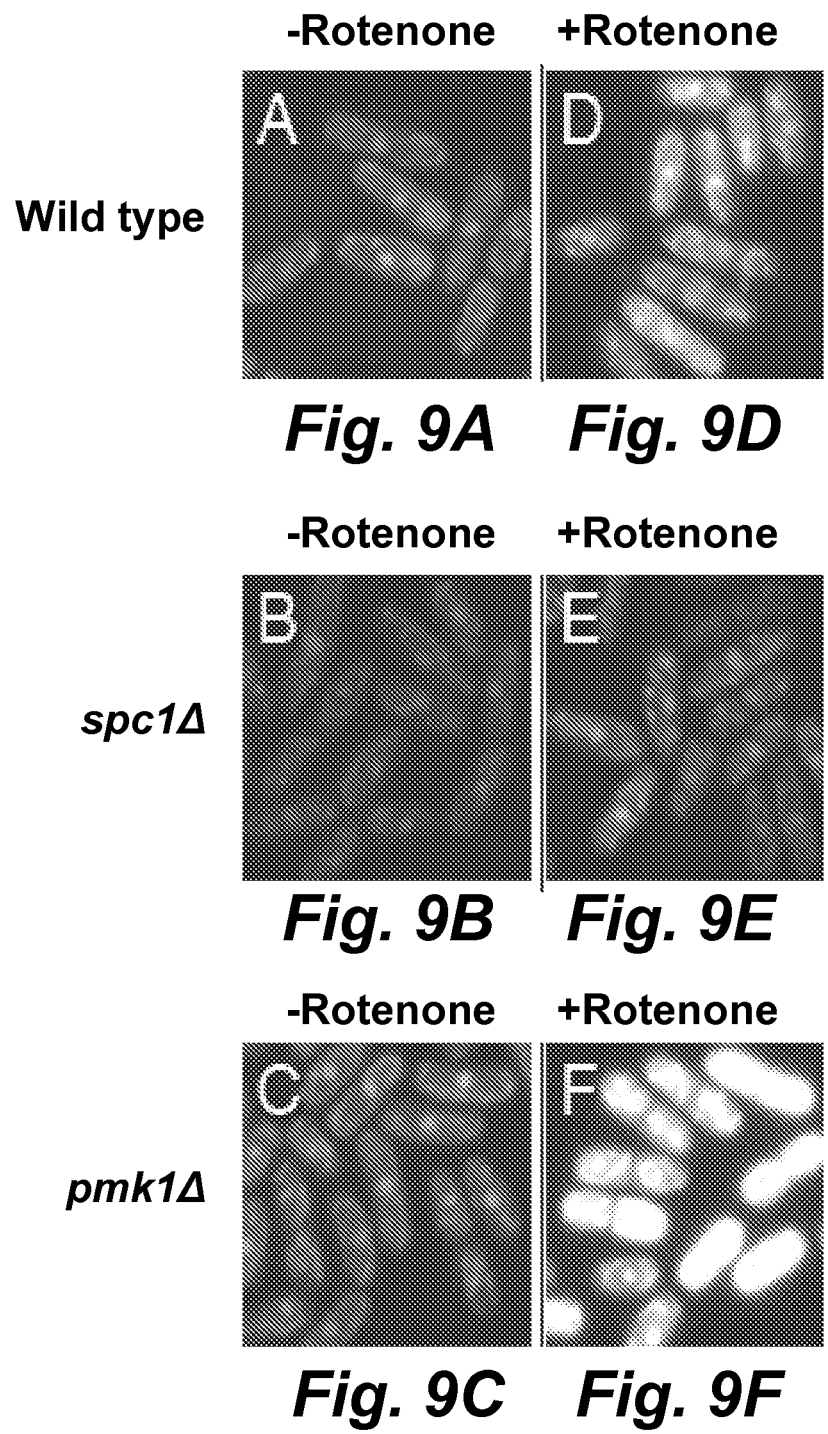

YEAST-BASED METHODS OF IDENTIFYING NUCLEIC ACIDS AND COMPOUNDS FOR TREATING NEURODEGENERATIVE DISEASES

CROSS-REFERENCE TO RELATED APPLICATION

This application claims priority to PCT Application No. US2009/065308, filed Nov. 20, 2009 and entitled "YEAST-BASED METHODS OF IDENTIFYING NUCLEIC ACIDS AND COMPOUNDS FOR TREATING NEURODEGENERATIVE DISEASES, and which also claims priority to U.S. Provisional Application No. 61/139,787," filed on Dec. 22, 2008, the entirety of which is herein incorporated by reference in its entirety.

STATEMENT REGARDING FEDERALLY SPONSORED RESEARCH OR DEVELOPMENT

This invention was made with government support under NIH Grant No.: R01GM068685 awarded by the U.S. National Institutes of Health of the United States government. The government has certain rights in the invention

TECHNICAL FIELD

The present disclosure is generally related to methods of screening nucleic acid and chemical libraries to identify agents having the potential to inhibit or reverse neurodegenerative diseases associated with mitochondrial dysfunction. The present disclosure, in particular relates to yeast-based screening methods.

BACKGROUND

Rotenone is a five-ring rotenoid compound found in the roots of several different plant species (Soloway (1976) Environ. Health Perspect. 14: 109-117). Likely used for centuries by indigenous peoples as a piscicide (fish poison) in the form of crude plant extracts and first purified more than a century ago, rotenone exhibits potent insecticidal, piscicidal, and pesticidal activities and is frequently used for these purposes (Ambrose & Haag (1936) Ind. Eng. Chem. Res. 28: 815-821; Geoffroy (1895) Ann. Inst. Colon. Marseille 2: 1-86; Soloway (1976) Environ. Health Perspect. 14: 109-117). Rotenone is listed as an active ingredient in more than forty commercially available pesticides approved for use by the U.S. Environmental Protection Agency.

It has been appreciated for some time that agricultural workers subjected to frequent pesticide exposure develop Parkinson's disease at a statistically higher rate than the general population, fueling suspicions that pesticides and other environmental toxins might contribute to the onset of this debilitating neurodegenerative disease, which afflicts as many as 1.5 million individuals in the United States alone (DeLong & Juncos (2005) In Harrison's Principles of Internal Medicine, D. Keal, ed. (New York, McGraw-Hill), pp. 2406-2418; Uversky (2004) Cell Tissue Res. 318: 225-241). It has also been shown that rats chronically treated with rotenone develop behavioral symptoms and pathophysiologies remarkably similar to those characteristic of human Parkinson's disease patients (Betarbet et al., (2000) Nat. Neurosci. 3: 1301-1306).

Rotenone is a specific inhibitor of complex 1 of the mitochondrial electron transport chain found in animal cells, which accounts for its pesticidal potency (Yagi et al., (1998) Biochim. Biophys. Acta 1364: 125-133). Dopaminergic neurons of rotenone-treated rats have been shown to exhibit mitochondrial abnormalities similar to those detected in the brains of deceased Parkinson's disease patients, including indications of complex I inhibition, and significant oxidative stress damage (Greenamyre et al., (2003) Parkinsonism Relat. Disord. 9 (Suppl 2): S59-64; Schapira, (2008) Lancet Neurol. 7: 97-109). While correlative evidence supports the notion that complex I inhibition might be at least partially responsible for dopaminergic cell death in idiopathic Parkinson's disease patients, evidence directly supportive of such a link has not been obtained. However, it has been shown that rotenone can induce dopaminergic neuron death independently of complex I, indicating the potential of complex I-independent mechanisms of rotenone-induced mitochondrial perturbation and cytotoxicity (Choi et al., (2008) Proc. Natl. Acad. Sci. U.S.A. 105:15136-15141).

Mitochondrial dysfunction is a primary or contributory factor in a broad range of neurological disorders and other human diseases, including Friedreich's ataxia, MALAS syndrome, and Barth syndrome, and is strongly implicated in the etiology of Parkinson's disease, a debilitating neurodegenerative disorder that afflicts millions of individuals worldwide. It is strongly suspected that most cases of sporadic Parkinson's disease, by far the most common form, arise from a combination of genetic predispositions and environmental factors, in particular exposures to pesticides and other environmental toxins. Supporting this hypothesis, it has been shown that prolonged treatment of rats with the widely used pesticide, rotenone, induces Parkinson's disease-like symptoms and pathophysiologies, including the mitochondrial dysfunction that is characteristic of the disease. While the rat-rotenone model now serves as an important tool for investigating the pathophysiology and potential treatment of Parkinson's disease, the system is not well suited for large-scale screens for identifying neuroprotective genes and drugs.

The fission yeast, *Schizosaccharomyces pombe*, and budding yeast, *Saccharomyces cerevisiae*, are species of fungi that do not possess the complex I components characteristic of animal cell mitochondria (Kerscher, (2000) Biochim. Biophys. Acta. 1459: 274-283). *S. cerevisiae* utilizes distinct NADH dehydrogenases, one exposed to the mitochondrial intermembrane space (Ndel) and the other to the mitochondrial matrix (Ndil), which allow for the oxidation of cytoplasmic and mitochondrial matrix NADH, respectively (Kerscher, (2000) Biochim. Biophys. Acta. 1459: 274-283). The *S. pombe* genome also encodes homologs Ndel and Ndil and it is presumed that they play roles analogous to their counterparts in budding yeast (Chiron, (2007) Methods Mol. Biol. 372: 91-105). Previous studies dating back to the early 1970s suggested that rotenone has little or no effect on mitochondrial function in either *S. pombe* or *S. cerevisiae* and it has since been largely accepted as dogma that both organisms have rotenone-resistant mitochondrial function (Chiron et al., (2007) Methods Mol. Biol. 372: 91-105; Kerscher, (2000) Biochim. Biophys. Acta. 1459: 274-283). While this dogma is supported by experimental evidence in the case of *S. cerevisiae*, the same cannot be claimed for *S. pombe*. The effects of rotenone on growth and mitochondrial function in this organism have been described only once (Heslot et al., (1970) J. Bacteriol. 104: 473-481), which showed that NADH dehydrogenase activity in this yeast is unaffected by relatively high concentrations of rotenone.

SUMMARY

Briefly described, embodiments of this disclosure, among others, encompass methods for the screening of small molecules or nucleic acids that may reverse the inhibition of growth of the unicellular yeast *Schizosaccharomyces pombe* by rotenone. The use of a yeast as the screening target allows for the high-throughput screening of small molecule and nucleic acid libraries for candidates that may then be screened in animal models as therapeutic agents for the treatment of neurodegenerative diseases.

The plant-derived isoflavonoid, rotenone, induces Parkinson's disease-like symptoms when chronically administered to rats, and death of dopaminergic neurons in culture. Although rotenone is a potent inhibitor of the multi-subunit NADH:ubiquinone oxidoreductase (complex I) of animal cell mitochondria, it can induce death of dopaminergic neurons independently of complex I inhibition. Mitochondria of the fission yeast, *Schizosaccharomyces pombe*, do not possess complex I but instead have distinct, nuclear genome encoded NADH dehydrogenases that are insensitive to rotenone.

Rotenone, while only moderately inhibitory to *S. pombe* cell growth on complex rich medium, is highly inhibitory to growth on synthetic minimal medium. The rotenone induces disruption of mitochondrial localization and generation of reactive oxygen species (ROS) in *S. pombe* cells. *S. pombe* cells carrying a deletion in the gene pmk1, which encodes an ERK-type MAP kinase required for resistance to the organic oxidant t-butyl hydroperoxide, are hypersensitive to rotenone. Cells carrying a deletion in spc1, which encodes a p38 MAP kinase homolog essential for survival of hydrogen peroxide-induced stress, exhibit rotenone resistance. Several additional genes required for rotenone resistance in *S. pombe* have been identified: the gene encoding cyclic AMP (cAMP)-dependent protein kinase (pka1), and gene aks1 encoding a protein required for normal mitochondrial and microtubule integrity. Moreover cells lacking Pmk1, but not Spc1, accumulate significantly higher levels of ROS in response to rotenone treatment than wild type *S. pombe* cells. *S. pombe*, therefore, provides a model for elucidating complex 1-independent targets of rotenone, and can serve as a screening tool for identifying compounds or oligonucleotides potentially able to reverse the effects of rotenone or Parkinson's disease in animal or human subjects.

One aspect of the present disclosure, therefore, encompasses methods of identifying a test compound that is characterized by its ability to reduce rotenone inhibition of the proliferation of a unicellular fungus, the methods comprising: (a) obtaining a culture of a strain of a unicellular fungus, where the proliferative status of the unicellular fungus when in contact with rotenone is reduced compared to the proliferative status of the unicellular fungus when not in contact with rotenone; (b) contacting the unicellular fungus in contact with rotenone with a test compound; and (c) determining whether the proliferative status of the unicellular fungus in contact with rotenone and with a test compound increases compared to the proliferative status of the unicellular fungus in contact with rotenone but not with a test compound, thereby indicating whether the test compound reduces inhibition of unicellular fungus cell proliferation by rotenone.

In the embodiments of this aspect of the disclosure, the unicellular fungus can be a strain of the yeast *Schizosaccharomyces pombe*.

In embodiments of this aspect of the disclosure, the unicellular fungus can be maintained under culture conditions comprising a limited nutrient minimal medium, whereby the proliferative status of the unicellular fungus when in contact with rotenone is reduced compared to the proliferative status of the unicellular fungus when not in contact with rotenone.

In other embodiments of this aspect of the disclosure, the strain of unicellular fungus may comprise a variant of a gene, said variant conferring sensitivity of the unicellular fungus to proliferative inhibition by rotenone. In some of these embodiments, the gene variant can be a variant of a gene encoding a mitochondrial component.

In embodiments of this aspect of the disclosure, the step of contacting the unicellular fungus in contact with rotenone with a test compound may comprise delivering to the unicellular fungus at least one test heterologous nucleic acid, and the method may further comprise the steps: (i) isolating a strain of the unicellular fungus receiving the test heterologous nucleic acid and having an increased proliferative status in the presence of rotenone as compared to the proliferative status of the untransformed unicellular fungus in contact with rotenone; and (ii) identifying the heterologous nucleic acid of the rotenone-resistant strain of the unicellular fungus, where said heterologous nucleic acid confers resistance to rotenone on the unicellular fungus.

In these embodiments, the at least one variant gene can be selected from the group consisting of: psd1, psd2, psd3, aks1, pmk1, and any combination thereof.

In one embodiment of this aspect of the disclosure, the unicellular fungus is a strain of the yeast *Schizosaccharomyces pombe*, and the genetic variation conferring sensitivity to rotenone comprises a mutation in the gene aks1, pmk1, or pka1.

In another embodiment of the disclosure, the unicellular fungus is a strain of the yeast *Schizosaccharomyces pombe*, and the genetic mutation conferring sensitivity to rotenone comprises a mutated variant of least one gene selected from the group consisting of: psd1, psd2, psd3, and any combination thereof.

Another aspect of the disclosure provides a method of identifying a test compound characterized by reducing rotenone inhibition of the proliferation of *Schizosaccharomyces pombe*, comprising: (a) culturing a strain of *Schizosaccharomyces pombe* in a limited nutrient minimal medium; (b) contacting the culture of *Schizosaccharomyces pombe* with rotenone thereby reducing the proliferative status of the *Schizosaccharomyces pombe* compared to the proliferative status of *Schizosaccharomyces pombe* when not in contact with rotenone; (c) contacting the *Schizosaccharomyces pombe* in contact with rotenone with a test compound; (d) determining the proliferative status of the *Schizosaccharomyces pombe*; and (e) determining whether the proliferative status of the *Schizosaccharomyces pombe* in contact with rotenone and with a test compound increases compared to the proliferative status of the *Schizosaccharomyces pombe* in contact with rotenone but not with a test compound, thereby indicating whether the test compound reduces inhibition of *Schizosaccharomyces pombe* proliferation by rotenone.

Still another aspect of the present disclosure provides methods of identifying a test compound characterized by reducing rotenone inhibition of the proliferation of *Schizosaccharomyces pombe*, comprising: (a) culturing a strain of *Schizosaccharomyces pombe*, wherein the strain of *Schizosaccharomyces pombe* comprises a variant of a gene, said variant conferring sensitivity of the *Schizosaccharomyces pombe* to proliferative inhibition by rotenone; (b) contacting the culture of *Schizosaccharomyces pombe* with rotenone, thereby reducing the proliferative status of the *Schizosaccharomyces pombe* compared to the proliferative status of *Schizosaccharomyces pombe* when not in contact with rotenone; (c) delivering to the *Schizosaccharomyces pombe* at least one test heterologous nucleic acid; (d) contacting the *Schizosaccharomyces pombe* with rotenone; (e) isolating a strain of the *Schizosaccharomyces pombe* receiving at least one test heterologous nucleic acid and having increased proliferative status in the presence of rotenone as compared to the proliferative status of the untransformed *Schizosaccharomyces pombe* in contact with rotenone; and (f) identifying the heterologous nucleic acid delivered to the rotenone-resistant strain of the *Schizosaccharomyces pombe*, wherein said heterologous nucleic acid confers resistance to rotenone on the *Schizosaccharomyces pombe*.

In embodiments of this aspect of the disclosure, the gene can be selected from the group consisting of: psd1, psd2, psd3, aks1, pmk1, and any combination thereof.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A: Wild-type *S. pombe* cells were cultured in YES liquid medium to midlog phase, harvested by centrifugation, and resuspended in YES medium at $5 \times 10^6$ cells/ml. The resulting cell suspension was serially diluted (1:5) and 3 μl of each dilution was spotted onto YES control medium (top panel) or YES supplemented with rotenone at the indicated concentrations. Plates were incubated for 3 days at 30° C. FIG. 1B: Wild-type *S. pombe* cells were cultured in YES liquid medium to mid-log phase, harvested by centrifugation, and resuspended in EMM medium at $5 \times 10^6$ cells/ml. The resulting cell suspension was serially diluted (1:5) and 3 μl of each dilution was spotted onto EMM control medium (top panel), or EMM supplemented with rotenone at the indicated concentrations. Plates were incubated for 4 days at 30° C.

FIG. 4 shows digital images of the growth of an spc1Δ strain of *S. pombe* cultured on complex YES medium containing 16 μM rotenone (+rotenone) or no rotenone (control). The *S. pombe* spc1Δ MAP kinase mutant is not hypersensitive to rotenone, showing that rotenone does not trigger a general oxidative stress, which is lethal to spc1Δ cells.

FIGS. 5A-5D show a series of digital images illustrating that rotenone induces fragmentation of mitochondrial localization in *S. pombe* cells. Wild-type *S. pombe* cells were cultured to mid-log phase in YES liquid medium and treated, or not, with rotenone (6.4 μg/ml) for 4 hrs. Control (FIG. 5A) and rotenone treated cells (FIG. 5B) were stained with MTGreen and visualized by fluorescence microscopy. Control cells were treated with a volume of DMSO equivalent to that used for rotenone treated cells FIG. 5C: DIC photomicrograph of wild type *S. pombe* cells cultured to mid-log phase in YES. FIG. 5D: DIC photomicrograph of wild type *S. pombe* cells cultured for 12 hr to mid-log in YES supplemented with rotenone (6.4 μg/ml).

FIGS. 9A-9F shows a series of digital images illustrating that Pmk1, but not Spc1, is required for normal clearance of rotenone-induced ROS in *S. pombe* cells. Wild type (FIGS. 9A and 9D), spc1Δ (FIGS. 9B and 9E), and pmk1Δ (FIGS. 9C and 9F) *S. pombe* strains were cultured to mid-log phase in YES liquid medium, treated (FIGS. 9D, 9E, and 9F), or not (FIGS. 9A, 9B, and 9C), with rotenone (6.4 μg/ml) for 12 hr, stained with DHE, and visualized by fluorescence microscopy. Control cells were treated with a volume of DMSO equivalent to that used for the rotenone-treated cells.

FIGS. 6A and 6B: untreated pmk1Δ (FIG. 10A) and spc1Δ (FIG. 10B) cells. FIGS. 10C and 10D: pmk1Δ (FIG. 10C) and spc1Δ (FIG. 10D) cells treated with rotenone (6.4 μg/ml) for 4 hr. Inset panel of FIG. 10B: an spc1Δ cell with abnormal mitochondrial aggregates.

Figures 1A, 1B:
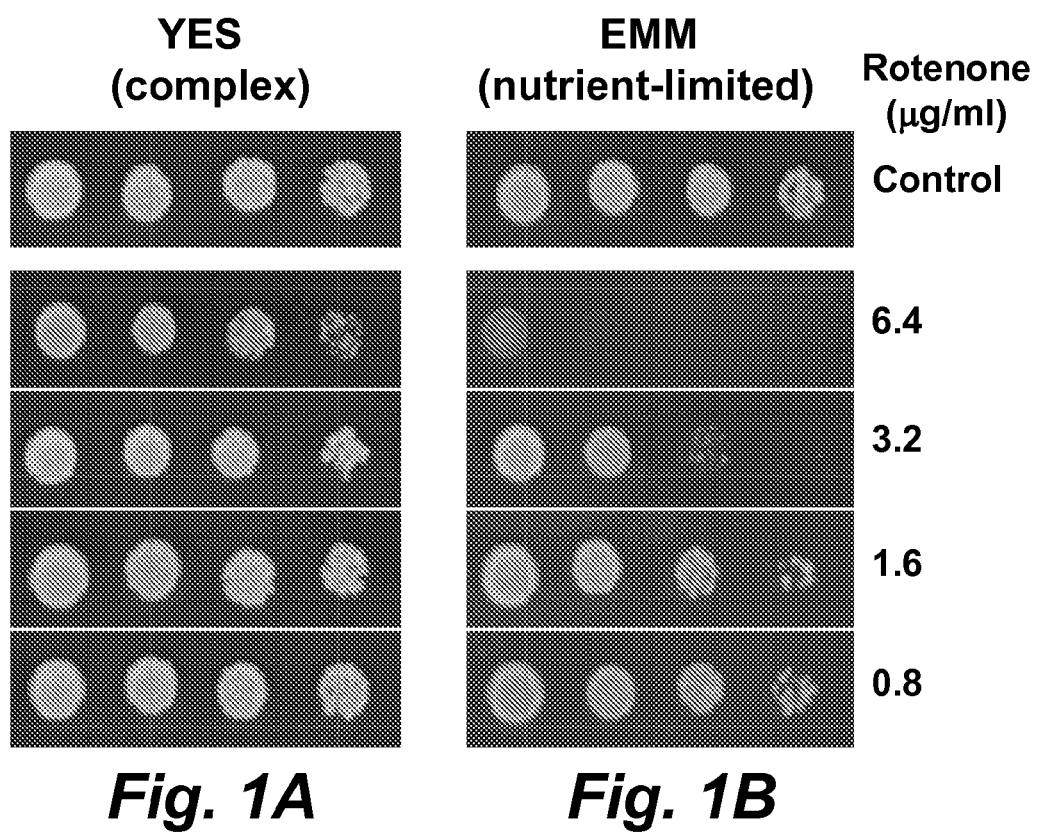
FIGS. 1A and 1B show a series of digital images illustrating the effects of rotenone on *S. pombe* cell growth under nutrient-enriched and nutrient limited conditions.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosed subject matter, the following terminology will be used in accordance with the definitions set forth below.

The term "neurological degenerative disease" as used herein refers to a broad range of neurological disorders and other human or animal diseases, including, but not limited to, Friedreich's ataxia, MALAS syndrome, and Barth syndrome, Parkinson's disease, and the like.

As used herein, "candidate compound" or "test compound" refers to any agent with a suspected potential to reduce, alleviate, prevent, or reverse a neurodegenerative disease in an animal or human patient. In particular, a "test compound" as used herein refers to any large or small molecule suspected of having the characteristic of being able to restore, in whole or in part, the proliferative status of a test unicellular fungus where growth of the fungus is limited due to exposure to rotenone or a derivative thereof. Potential therapeutic agents will be recognized as having the potential in vivo to reduce, alleviate, prevent, or reverse at least one symptom of a neurodegenerative disease in an animal or human patient. The term "potential therapeutic agent" as used herein need not actually exhibit therapeutic efficacy in vivo: since candidate compounds identified as having substantial activity on yeast cells in vitro are useful, e.g., for the elucidation of structure-activity relationships associated with suppression of toxicity in cells, these agents can be used for the further development of a therapeutic agent that can substantially retain the ability (or has an improved ability) to inhibit degeneration in a cell, and especially in a neural cell, but which also has, relative to the originally identified agent, other properties better suited for in vivo use (for example, increased stability, increased cellular uptake, or other properties which provide for a more favorable pharmacokinetic and/or pharmacodynamic profile).

Many types of candidate, or test, compound can be screened by the methods according to the present invention. Suitable candidate compounds include, for example, small molecules, nucleic acids, peptides, peptidomimetics, synthetic compounds and/or natural compounds. A candidate compound can be contacted with the cell according to the characteristics of the candidate compound and the cell. A cell can be contacted with, or receive, a nucleic acid by such as, but not limited to, transformation. A cell also can be contacted with a candidate compound by culturing the cell in media containing the candidate compound. For example, a yeast cell can be contacted with a candidate compound by culturing the cell in liquid media, or growing the cell on solid or semi-solid media containing the candidate compound. In certain embodiments, the cell wall of a yeast cell can be partially removed to generate a spheroplast, and the spheroplast contacted with the candidate compound. The spheroplasts optionally can regenerate in the presence of the candidate compound.

The term "rotenone" as used herein is a common name for the compound having the IUPAC name 2R,6aS,12aS)-1,2,6,6a,12,12a-hexahydro-2-isopropenyl-8,9-dimethoxy-chromeno[3,4-b]furo(2,3-h)chromen-6-one. Alternative names for this compound include Tubatoxin and Paraderil.

The term "unicellular fungus" as used herein refers to a typically unicellular fungus such as a yeast that reproduces asexually. The term "yeast" may also refers to an array of yeasts. The term is not meant to exclude species which have yet to be discovered but may later be identified and included in this definition by those of skill in the art. The term "yeast" includes one or more species of the following organisms: *Candida* spp., *Kluyveromyces* spp., *Cryptococcus* spp., *Pichia* spp., *Torulaspora* spp., *Saccharomyces* spp., including but not limited to, *Saccharomyces cerevisiae*, and *Zygosacchromyces* spp. In particular, the terms "unicellular fungus" and yeast as used herein refer to strains and mutants of the species *Schizosaccharomyces pombe* (*S. pombe*).

The term "proliferative status" as used herein refers to the degree of population expansion occurring at a time point, whether the population is increasing (proliferation), is static (stasis), or declining. Comparison of the proliferative status at one time point with that at an earlier time point allows determination of whether the growth or proliferation of a cell population may be increasing (proliferation enhancement), decreasing (such as due to proliferation inhibition), or static (such as due to proliferation inhibition). Comparison of the proliferative status of an organism or cell under one growth condition such as in the presence of a test compound, with the proliferative status under a second growth condition such as the abcence of the test compound allows determination of whether the growth or proliferation of a cell population may be increased (proliferation enhancement), decreased (such as due to proliferation inhibition), or static (such as due to proliferation inhibition) due to the presence of the test compound.

The term "sensitivity to rotenone" as used herein refers to a response by a strain of a yeast on exposure to rotenone in a culture medium. The sensitivity may be manifested as a change in the proliferative status of the yeast culture, and in particular inhibition of cell proliferation.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "mutation" as used herein refers to a change in nucleic acid sequence or an amino acid sequence that causes the sequence to differ from another. The mutation may be a substitution, an addition, or a deletion of one or more consecutive or non-consecutive nucleotides or amino acids from the parent nucleotide or amino acid sequence. A deletion from a sequence may be denoted by the symbol "Δ" or the abbreviation "del".

The terms "transformation" and "transfection" as used herein are intended to refer to a variety of art-recognized techniques for introducing foreign nucleic acid (e.g., DNA) into a host yeast cell, including calcium phosphate or calcium chloride co-precipitation, lithium acetate transformation, DEAE-dextran-mediated transfection, lipofection, or electroporation. It is contemplated that a heterologous nucleic acid may be delivered to a cell such as a yeast cell by inclusion of the nucleic acid sequence in a vector such as a viral vector, a plasmid vector, an artificial chromosome, and the like. It is further contemplated that the heterologous nucleic acid sequence may be operably linked to an expression control element such as, but not limited to, a promoter whereby the nucleic acid sequence may be expressed as an RNA molecule or as a polypeptide product.

The term "culture medium" as used herein refers to a solid or liquid medium comprising sufficient nutrients, including at least one carbon source, on which a microorganism (e.g., a yeast) can grow. In chemostat or batch cultures the medium is a liquid.

The term "carbon source" as used herein refers to an organic compound (e.g., glucose) or a mixture of organic compounds, which can be assimilated by a microorganism (e.g., yeast) and used to make new cell material.

The term "minimal media" or "synthetic media" as used herein refers to culture media for growing a microorganism (e.g., yeast) that comprises a nitrogen source, salts, trace elements, vitamins, and a carbon source, which are all defined. The carbon source can comprise at least one of glucose, sucrose, lactose, galactose, or fructose, among others. Synthetic media do not comprise for example, a nutrient source, whose composition is not defined, such as corn steep liquor, yeast extract or peptone, among others, which can be used in complex culture media. In certain embodiments, the mineral medium may comprise $(NH_4)_2SO_4$; $KH_2PO_4$; $MgSO_4$; EDTA; $ZnSO_4$; $CoCl_2$; $MnCl_2$; $CuSO_4$; $CaCl_2$; $FeSO_4$; $Na_2MoO_4$; $H_3BO_3$; KI; and optionally an antifoam agent.

The term "rich culture medium" as used herein refers to a culture medium where the nutrient amounts are not limiting, and allow the yeast to grown until factors other than the supply of nutrients, prevents further growth.

The term "capable of growing on a solid culture medium" as used herein refers to the ability of a microorganism (e.g., yeast) that has been streaked or spread on solidified culture medium so that colonies are not visible to the naked eye to produce at least one colony visible to the naked eye, after incubation in a suitable environment (e.g., pH and temperature among others) for a period of time.

The term "capable of growing in a liquid culture medium" as used herein refers to the ability of a microorganism (e.g., yeast) that is introduced into a liquid culture medium under appropriate culture conditions (e.g., pH and temperature, among others) to replicate such that the biomass of the culture increases during the growth phase of the culture.

Description

The present disclosure encompasses methods for identifying compounds or genetic elements that may reverse the sensitivity of a unicellular yeast to proliferation inhibition that is induced by exposure to rotenone. The embodiments of the present disclosure are based on the discovery of the sensitivity to rotenone of the yeast *S. pombe* when under conditions of nutritional limitation, or of mutant strains of *S. pombe* where the mutations are of genes associated with the functioning of mitochondria. The sensitivity of *S. pombe* to rotenone under certain conditions provides an indicator that is analogous to the cellular damage or malfunctions associated with neurodegenerative diseases such as Parkinson's disease. Embodiments of the methods of the present disclosure provide methods to rapidly screen nucleic acid or small molecule libraries for potential candidates that may be more specifically screened as therapeutic agents to counteract the cytopathological characteristics of such as Parkinson's disease.

The methods of the present disclosure can comprise culturing a unicellular yeast such as *S. pombe* under conditions of nutritional limitation, whereupon the cells become sensitive to proliferation inhibition induced by rotenone. In one embodiment of the assays of the disclosure, exposure of the cells cultured under nutritionally stressful conditions to compounds such as, but not limited to, small molecule antioxidants may reverse rotenone inhibition.

In other embodiments of the assays of the disclosure, a gene mutation such as, but not limited to, a deletion within a gene encoding phosphotidylserine decarboxylase (psd1Δ, psd2Δ, psd3Δ, and any combination thereof) may be introduced into the yeast cells such that the small molecule test compounds may be directed to interacting to a particular biochemical or physiological pathway that may reverse rotenone inhibition. In still other embodiments of the assay methods of the disclosure, mutations may be introduced into the unicellular yeast *S. pombe* and which, by generating mitochondrial defects also confer sensitivity to rotenone. Such strains of mutated yeast may be used in the assays of the disclosure to identify nucleic acid molecules that may reverse such mutations, thereby restoring resistance to rotenone inhibition.

The lipophilic pesticide, rotenone, is a potent inhibitor of complex I of the electron transport chain found in animal cells, and induces Parkinson's disease-like behavioral symptoms and pathophysiologies when chronically administered to rats (Greenamyre et al., (2003) *Parkinsonism Relat. Disord.* 9 (Suppl 2): S59-64; Schapira, (2008) *Lancet Neurol.* 7; 97-109). It is likely that the observed pathophysiological effects, however, are independent of complex I inhibition.

Like a number of other fungal species, the fission yeast, *Schizosaccharomyces pombe*, does not possess complex I of the electron transport chain found in the mitochondria of animal cells. It has been assumed, therefore, that rotenone had little or no effect on either mitochondrial function or cell growth in this organism. However, rotenone only modestly inhibits growth of wild type *S. pombe* cells in nutrient-rich conditions; it is profoundly inhibitory to cell growth in nutrient-limited conditions.

Similar to its effects on mammalian cells, rotenone treatment results in the generation of high levels of reactive oxygen species (ROS) in *S. pombe* cells. As described in the Examples below, and in the accompanying figures, resistance to rotenone in *S. pombe* is dependent on components of the cyclic AMP-protein kinase A (PKA) system, but not on the MAP kinase Spcl/Styl that is required for hydrogen peroxide-induced oxidative stress response and survival in this organism (see, for example, FIGS. 2 and 4).

Yeast *S. cerevisiae* and *S. pombe* have related nuclear genes encoding two types of single polypeptide NADH dehydrogenases, which are insensitive to rotenone (Joseph-Horne et al., (2001) *Biochim. Biophys. Acta* 1504: 179-195; Chiron et al., (2007) *Methods Mol. Biol* 372: 91-105; and Heslot et al., (1970) *J. Bacteriol.* 104: 473-481). Rotenone, while only modestly inhibitory to growth of *S. pombe* cells on complex rich medium, is substantially more inhibitory to growth on synthetic defined minimal medium, as shown in the Examples, below. Rotenone induces disruption of mitochondrial localization and generation of ROS in *S. pombe* cells, which has also been seen in mammalian cells (Li et al., (2003) *J. Biol. Chem.* 278: 8516-8525). Rotenone, therefore, can induce the disruption of mitochondrial organization and generation of ROS in a eukaryote (yeast) that naturally lacks the class I NADH:ubiquinone oxidoreductase complex found in animal cell mitochondria.

Since rotenone induces the accumulation of ROS in wild type *S. pombe* cells, it was determined whether a second stress-responsive MAPK in this organism, Pmk1, is required for rotenone resistance. Unlike spc1Δ cells, pmk1Δ cells were hypersensitive to the growth inhibitory effects of rotenone. Further, pmk1Δ cells, but not spc1Δ cells, accumulate greater concentrations of ROS than wild type *S. pombe* cells in response to rotenone exposure. In comparison to wild type *S. pombe* cells, spc1Δ-bearing cells exhibit resistance to rotenone as measured by effects of the toxin on cell growth, mitochondrial localization, and production of ROS. These findings indicate that spc1Δ cells are physiologically sensitized to more rapidly respond and/or adapt to the molecular consequences of rotenone exposure. In this regard, it has been shown that Pmk1, while exhibiting a similar level of activity in wild type and spc1Δ cells in low stress culturing conditions, is both hyperactivated and undergoes a slower rate of deactivation in response to hyperosmotic shock in spc1Δ cells relative to wild type *S. pombe* cells (Madrid et al., (2006) *J Biol Chem* 281: 2033-2043). This finding indicates that in spc1Δ cells the regulatory network regulating Pmk1 activation is hyper-responsive to physiological stresses that induce the protein kinase.

In several different types of mammalian cells, rotenone can induce fragmentation of mitochondrial organization, which in neurons, fibroblasts, and possibly other mammalian cell types, maintain tubular organizations bearing some resemblance to mitochondrial localization in *S. pombe* cells (Barsoum et al., (2006) *EMBO J.* 25: 3900-3911; Amchenkova et al., (1988) *J. Cell Biol.* 107: 481-495; Benard et al., (2007) *J. Cell Sci.* 120: 838-848; Plecita-Hlavata et al., (2008) *Biochim. Biophys. Acta* 1777: 834-846). The data of the present disclosure indicate that rotenone induces disruption of mitochondrial localization in an organism, *S. pombe*, that naturally lacks complex I, demonstrating that the toxin can disrupt mitochondrial localization independently of complex I inhibition.

The mechanism(s) by which rotenone inhibits complex I in animal cell mitochondria has yet to be definitively elucidated. Results of photoaffinity labeling experiments have suggested that it may interact directly with the ND1 and PSST components of complex I as well as other constituents in mitochondrial preparations (Schuler & Casida (2001) *Biochim. Biophys. Acta* 1506: 79-87; Nicolaou, K., Pfefferkorn et al., (2000) *Chem. Biol.* 7: 979-992). The latter finding is consistent with evidence that rotenone may interact with both protein and lipid components of mitochondria (Gutman et al., (1970) *Proc. Natl. Acad. Sci. U.S.A.* 65: 763-770). The data of the present disclosure show that rotenone has profound effects on mitochondrial integrity in *S. pombe* and this genetically tractable organism provides a useful model for gaining insights regarding complex I-independent mitochondrial targets of rotenone in eukaryotic cells.

Embodiments of the present disclosure exploit the sensitivity of *S. pombe* to rotenone that occurs when the cells are cultivated on nutrionally-limiting (minimal) medium. The embodiments of the disclosure provide assays for identifying small molecule candidate compounds that may reverse the rotenone-induced inhibition of S. pombe proliferation. Additionally, S. pombe may be transformed by nucleic acid molecules, using methods known to those in the art, and subsequently cultured on nutritionally-limiting rotenone-containing selective medium. Yeast cells that proliferate on such medium may then be isolated and the heterologous nucleic acid identified as a potential antagonist of rotenone-induced inhibition of yeast growth.

In addition to the use of minimal medium to allow rotenone-induced inhibition of wild-type S. pombe growth, embodiments of the present disclosure may also employ S. pombe strains bearing mutations in genes associated with mitochondria structure or function. These mutants can also be sensitive to rotenone, even when cultured on complex medium such as YES medium.

Figure 2:
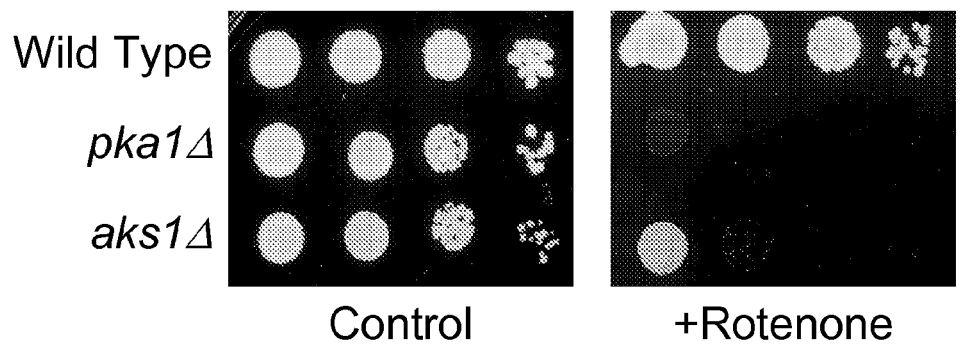
FIG. 2 shows digital images of the growth of three strains (wild-type, pka1Δ, and aks1Δ) of *S. pombe* cultured on complex YES medium containing 16 μM rotenone (+rotenone) or no rotenone (control). A deletion mutation of genes pka1 or aks1 confers sensitivity of the yeast to rotenone.

For example, as shown in FIG. 2, S. pombe mutant variants bearing a deletion mutation in the protein kinase A-encoding gene, pka1, or mutants carrying a deletion in the pka1-interacting gene aks1, and grown on complex (complete) YES medium, are both strongly hypersensitive to rotenone. Additionally, the yeast deletion mutants pka1Δ and aks1Δ exhibit significant mitochondrial abnormalities.

Figure 3:
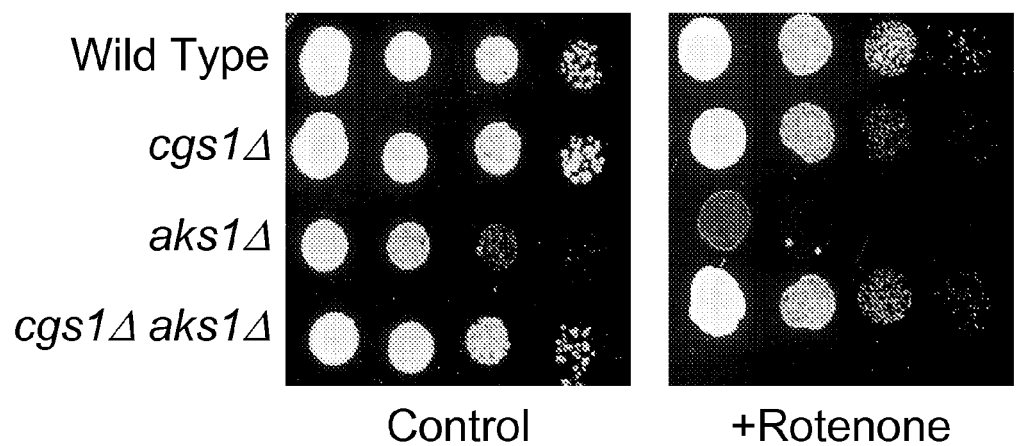
FIG. 3 shows digital images of the growth of four strains (wild-type, cgs1Δ, aks1Δ, and cgs1Δaks1Δ) of *S. pombe* cultured on complex YES medium containing 16 μM rotenone (+rotenone) or no rotenone (control). The deletion mutation of aks1 confers sensitivity of the yeast to rotenone. Deletion mutation cgs1Δ does not significantly increase the sensitivity of the cells to rotenone. However, cgs1Δ overrides the rotenone sensitivity conferred by aks1Δ, allowing the yeast to proliferate in the presence of rotenone.

In strain S. pombe aks1Δ, where there remains a functional PKA-expressing gene, the deletion mutation csg1Δ eliminates regulatory control of PKA function, and results in the elevation of PKA enzyme activity. The increase in PKA activity in csg1Δ aks1Δ double mutant cells restores rotenone resistance, as shown in FIG. 3, indicating that Pka1p (the protein product of the gene pka1) and Aks1p (the protein product of the gene aks1) act on one or more common molecular targets. Accordingly, by introducing a new genetic condition into the strain of S. pombe having the aks1Δ mutation, the effect of the deletion mutation aks1Δ to introduce sensitivity to rotenone, is overridden.

Figure 6:
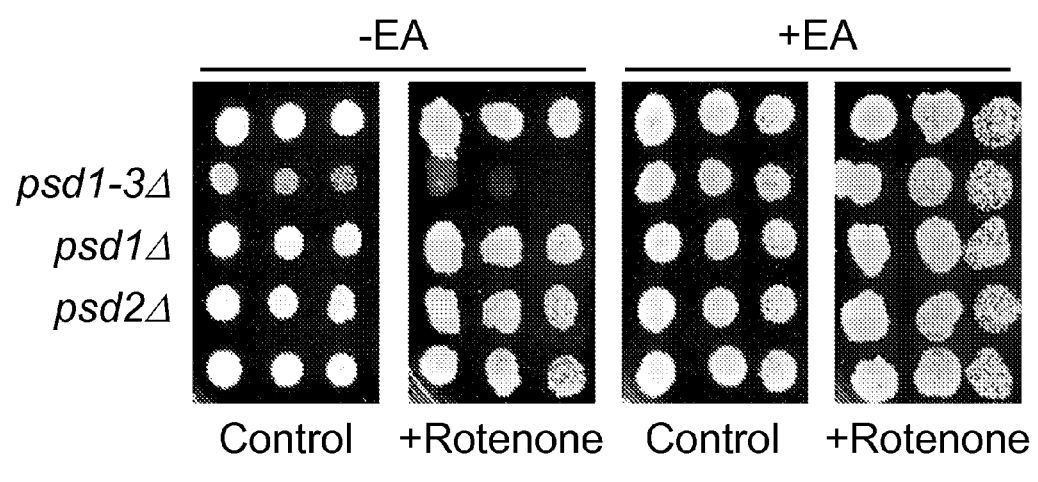
FIG. 6 shows digital images of the growth of five strains (wild-type, triple mutant psd1-3Δ, psd1Δ, psd2Δ, and psd3Δ) of *S. pombe* cultured on complex YES medium containing 16 μM rotenone (+rotenone) or no rotenone (control), and without (–EA) and with (+EA) 1 mM ethanolamine. Phosphatidylethanolamine (PE) deficiency results in a rotenone-sensitive phenotype that can be suppressed by ethanolamine. Log phase cultures were suspended at $10^7$ cells/ml, serially diluted (1:10), and spotted (5 μl per spot) onto YES (Control) or YES containing 16 μM rotenone (+Rotenone).

In embodiments of methods of the disclosure, therefore, a genetically modified S. pombe may be used to detect potential candidate small molecules that may reverse or over-ride the effects of rotenone. For example, but not intended to be limiting, the introduction into S. pombe of the triple deletion of genes encoding phosphotidylserine decarboxylase (psd1Δ, psd2Δ, and psd3Δ) results in the increased sensitivity of the yeast to rotenone, even when cultured on a complex medium. This sensitivity to rotenone may be reversed, for example, by the addition of ethanolamine, as shown in FIG. 6.

In another example of the reversal of rotenone inhibition of the proliferation of S. pombe, strains having a deletion mutation in the MAP kinase-encoding gene spc1 (spc1Δ) are not hypersensitive to rotenone, as shown in FIG. 4, indicating that rotenone is not triggering a general oxidative stress, which would be lethal to spc1Δ cells. However, wild-type S. pombe may be inhibited by rotenone when grown under nutrient stressed conditions, and ascorbic acid (an antioxidant) reversed rotenone-induced proliferation inhibition of both wild-type and pka1Δ S. pombe cells, indicating that rotenone may induce mitochondrial oxidative stress in this organism. Oxidative stress has been detected in the brains of deceased Parkinson's disease patients, and in rats exposed to rotenone as a model for Parkinson's disease.

The experimental data of the present disclosure demonstrate that S. pombe provides a useful model organism for gaining insights into complex 1-independent mechanisms by which rotenone perturbs mitochondrial function in eukaryotic cells, and which may be insightful with regard to the etiology of Parkinson's disease. In particular, the S. pombe rotenone toxicity systems described here are amenable to genetic and small molecule screenings that would identify potential therapeutic targets and therapeutic agents for the treatment of Parkinson's disease and other neurodegenerative disorders in which mitochondrial dysfunction is causative or contributory to disease pathology.

Embodiments of the present disclosure, therefore, provide screening assays for the detection and identification of small molecules that may relieve the effects of rotenone on a target yeast strain. The yeast may be grown on nutritionally-limiting (minimal) medium containing an inhibitory amount of rotenone. The medium may also contain an amount of a candidate compound to be tested for its ability to reverse the effects of the rotenone on the yeast. It is contemplated that the assay maybe configured for screening a plurality of candidate compounds, such as a small molecule library. For example, and not intended to be limiting, a culture plate of the yeast may be spotted with a plurality of candidate compounds from such as a library of compounds, and the efficacy of a candidate to reverse the rotenone effect is indicated by growth of the yeast on or around the candidate spot. In another embodiment of a screening assay, the yeast may be cultured in a liquid nutritionally-limiting medium, including an inhibitory amount of rotenone, and the candidate compound and growth detected by such as an increase in the optical density of the culture. It is intended that once a molecule has been identified as reversing in whole or in part yeast proliferation inhibition by rotenone, the candidate molecule may be further tested in animal models for its ability to reverse the effects of rotenone, thereby providing a potential therapeutic agent for the treatment of a neurological disorder.

It is also contemplated that the use of a yeast, and in particular, strains of the yeast Schizosaccharomyces pombe may be used for the screening of large test molecules such as oligonucleotides that may reverse the effects of a genetic mutation in a gene, the mutational variation conferring sensitivity of the yeast to proliferation inhibition by rotenone. In such screening assays, the test compound, i.e. the nucleic acid molecule is delivered to the variant strain of yeast by methods known in the art. For example, but not intended to be limiting, the nucleic acid may be delivered by transformation into yeast spheroplasts, by inclusion in a vector nucleic acid, and the like. It is also considered possible for the nucleic acid sequence to be an expressed sequence that may be an RNA, or the expressed polypeptide encoded therein.

Once the heterologous nucleic acid has been delivered to the yeast test organism, the yeast may be exposed to an amount of rotenone that can inhibit the proliferation of the yeast not receiving a test nucleic acid. A strain of the test yeast may then be identified and isolated based on the ability of the strain to proliferate in the presence of rotenone. The heterologous nucleic acid sequence responsible for conferring on the yeast resistance to rotenone may the n be isolated and characterized.

One aspect of the present disclosure, therefore, encompasses methods of identifying a test compound that is characterized by its ability to reduce rotenone inhibition of the proliferation of a unicellular fungus, the methods comprising: (a) obtaining a culture of a strain of a unicellular fungus, where the proliferative status of the unicellular fungus when in contact with rotenone is reduced compared to the proliferative status of the unicellular fungus when not in contact with rotenone; (b) contacting the unicellular fungus in contact with rotenone with a test compound; and (c) determining whether the proliferative status of the unicellular fungus in contact with rotenone and with a test compound increases compared to the proliferative status of the unicellular fungus in contact with rotenone but not with a test compound, thereby indicating whether the test compound reduces inhibition of unicellular fungus cell proliferation by rotenone.

In the embodiments of this aspect of the disclosure, the unicellular fungus can be a strain of the yeast *Schizosaccharomyces pombe*.

In embodiments of this aspect of the disclosure, wherein the unicellular fungus can be maintained under culture conditions comprising a limited nutrient minimal medium, whereby the proliferative status of the unicellular fungus when in contact with rotenone is reduced compared to the proliferative status of the unicellular fungus when not in contact with rotenone.

In other embodiments of this aspect of the disclosure, the strain of unicellular fungus may comprise a variant of a gene, said variant conferring sensitivity of the unicellular fungus to proliferative inhibition by rotenone. In some of these embodiments, the gene variant can be a variant of a gene encoding a mitochondrial component.

In embodiments of this aspect of the disclosure, the step of contacting the unicellular fungus in contact with rotenone with a test compound may comprise delivering to the unicellular fungus at least one test heterologous nucleic acid, and the method may further comprise the steps: (i) isolating a strain of the unicellular fungus receiving the test heterologous nucleic acid and having increased proliferative status in the presence of rotenone as compared to the proliferative status of the untransformed unicellular fungus in contact with rotenone; and (ii) identifying the heterologous nucleic acid of the rotenone-resistant strain of the unicellular fungus, where said heterologous nucleic acid confers resistance to rotenone on the unicellular fungus.

In these embodiments, the at least one variant gene can be selected from the group consisting of: psd1, psd2, psd3, aks1, pmk1, and any combinations thereof.

In one embodiment of this aspect of the disclosure, the unicellular fungus is a strain of the yeast *Schizosaccharomyces pombe*, and the genetic variation conferring sensitivity to rotenone comprises a mutation in the genes aks1 or pmk1.

In another embodiment of the disclosure, the unicellular fungus is a strain of the yeast *Schizosaccharomyces pombe*, and the genetic mutation conferring sensitivity to rotenone comprises a mutated variant of least one gene selected from the group consisting of: psd1, psd2, psd3, and any combination thereof.

Another aspect of the disclosure provides a method of identifying a test compound characterized by reducing rotenone inhibition of the proliferation of *Schizosaccharomyces pombe*, comprising: (a) culturing a strain of *Schizosaccharomyces pombe* in a limited nutrient minimal medium; (b) contacting the culture of *Schizosaccharomyces pombe* with rotenone thereby reducing the proliferative status of the *Schizosaccharomyces pombe* compared to the proliferative status of *Schizosaccharomyces pombe* when not in contact with rotenone; (c) contacting the *Schizosaccharomyces pombe* in contact with rotenone with a test compound; (d) determining the proliferative status of the *Schizosaccharomyces pombe*; and (e) determining whether the proliferative status of the *Schizosaccharomyces pombe* in contact with rotenone and with a test compound increases compared to the proliferative status of the *Schizosaccharomyces pombe* in contact with rotenone but not with a test compound, thereby indicating whether the test compound reduces inhibition of *Schizosaccharomyces pombe* proliferation by rotenone.

Still another aspect of the present disclosure provides methods of identifying a test compound characterized by reducing rotenone inhibition of the proliferation of *Schizosaccharomyces pombe*, comprising: (a) culturing a strain of *Schizosaccharomyces pombe*, wherein the strain of *Schizosaccharomyces pombe* comprises a variant of a gene, said variant conferring sensitivity of the *Schizosaccharomyces pombe* to proliferative inhibition by rotenone; (b) contacting the culture of *Schizosaccharomyces pombe* with rotenone, thereby reducing the proliferative status of the *Schizosaccharomyces pombe* compared to the proliferative status of *Schizosaccharomyces pombe* when not in contact with rotenone; (c) delivering to the *Schizosaccharomyces pombe* at least one test heterologous nucleic acid; (d) contacting the *Schizosaccharomyces pombe* with rotenone; (e) isolating a strain of the *Schizosaccharomyces pombe* receiving at least one test heterologous nucleic acid and having increased proliferative status in the presence of rotenone as compared to the proliferative status of the untransformed *Schizosaccharomyces pombe* in contact with rotenone; and (f) identifying the heterologous nucleic acid delivered to the rotenone-resistant strain of the *Schizosaccharomyces pombe*, wherein said heterologous nucleic acid confers resistance to rotenone on the *Schizosaccharomyces pombe*.

In embodiments of this aspect of the disclosure, the gene can be selected from the group consisting of: psd1, psd2, psd3, aks1, pmk1, and any combinations thereof.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include $\pm 1\%$, $\pm 2\%$, $\pm 3\%$, $\pm 4\%$, $\pm 5\%$, $\pm 6\%$, $\pm 7\%$, $\pm 8\%$, $\pm 9\%$, or $\pm 10\%$, or more of the numerical value(s) being modified.

EXAMPLES

Example 1

Yeast strains, media, and genetic methods. The following S. pombe strains were used in this study: SP870 (h90 ade6-210 leu1-32 ura4-D18), SPSPC1 U90 (h90 ade6-210 leu1-32 ura4-D18 spc1::ura4), SPM1L (h90 leu1-32 ura4-D18 spm1::LEU2). S. pombe cultures were grown in either YES medium (0.5% yeast extract; 3% dextrose; and adenine, histidine, leucine, lysine and uracil, each at 250 mg/L) or Edinburgh minimal medium (EMM) containing required auxotrophic supplements (Alfa et al., (1993) *Experiments with fission yeast: A laboratory course manual*, Cold Spring Harbor Laboratory Press, Cold Spring Harbor, N.Y., incorporated herein by reference in its entirety). Agar media contained 2% Bacto agar (Difco).

Example 2

Rotenone sensitivity assay. Rotenone stock solutions (10 mM in DMSO) were prepared just prior to carrying out each experiment and protected from light. Rotenone containing YES and EMM agar media were prepared by mixing rotenone stock solution with growth medium as required for the desired rotenone concentration (up to 6.4 µg/ml). For agar media, rotenone stock solution was added after autoclaving and cooling of the media to approximately 45° C. DMSO was added to control media at concentrations equivalent to that in media supplemented with rotenone. Plates were incubated at room temperature for 3-12 hr prior to use. S. pombe strains were cultured overnight in YES liquid medium at 30° C. to mid-log phase, concentrated to $5 \times 10^6$ cells/ml, and serially diluted (1:5). Three µl of each dilution was spotted onto rotenone containing plates and control plates and the plates were incubated at 30° C. for 2-4 days, as indicated in relevant figure legends.

Example 3

MitoTracker Green FM and dihydroethidium (DHE) staining of S. pombe cells. Mitochondrial localization was detected by staining S. pombe cells with MitoTracker Green FM (MTGreen) based on the protocol recommended by the manufacturer (Invitrogen). Briefly, S. pombe cells were cultured overnight in YES liquid medium at 30° C. to mid-log phase. Where indicated, rotenone stock solution was added to portions of each culture to a final concentration of 6.4 µg/ml. Equivalent volumes of DMSO were added to control cultures. Stock solutions of MTGreen (5 µM in DMSO) were prepared just prior to use. Staining was carried out by adding 10 µl of MTGreen stock solution to 1 ml of cell culture and incubating at 30° C. with shaking for 20 min. Stained cells were washed once with YES and resuspended in approximately 10 µl of YES prior to preparation of samples for microscopy. Stained cells were concentrated by centrifugation to a volume of approximately 10 µl. DHE staining was carried out as described by Huard et al., (2008) *Cell Res.* 18: 961-973, incorporated herein by reference in its entirety. Stained cells were visualized by epifluorescence microscopy using a Nikon 90i automated epifluorescence microscope system operated using Nikon NIS-Elements software. Images were captured using a CoolSNAP HQ2 monochrome CCD camera (Photometrics). RAW images were level-adjusted using the Adobe PhotoShop CS3 software application.

Example 4

Effects of rotenone on S. pombe cell growth in nutrient-enriched and nutrient-limited conditions. To investigate the effects of rotenone on S. pombe cell growth, we prepared complex rich (YES) and synthetic defined minimal (EMM) agar media containing concentrations of rotenone ranging from 0.2 to 6.4 µg/ml. This range of rotenone concentration started just below that (0.3 µg/ml) described previously as having a negligible effect on S. pombe cell growth (Heslot et al., (1970) *J Bacteriol* 104: 473-481). Since rotenone has a relatively short half-life in aqueous solutions, growth media containing the toxin were prepared freshly prior to each experiment. Mid-log phase cultures of wild type S. pombe cells were serially diluted and tested for growth on YES and EMM plates containing rotenone and on control media lacking the toxin. As shown in FIG. 1A, modest inhibition of S. pombe growth was detectable on YES medium containing 6.4 µg/ml rotenone but not on YES containing lower concentrations of the toxin. In contrast, we found that on EMM minimal medium, S. pombe growth was strongly inhibited by 6.4 µg/ml rotenone and slightly inhibited by a concentration as low as 1.6 µg/ml (FIG. 1B). These results demonstrate that rotenone can, indeed, inhibit S. pombe cell growth and that it is more inhibitory in nutrient limited conditions than in nutrient-enriched conditions.

Example 5

Rotenone induces disruption of mitochondrial localization in S. pombe cells. Similar to some mammalian cells, such as fibroblasts and nerve cells (Barsoum et al., (2006) *EMBO J.* 25: 3900-3911; Amchenkova et al., (1988) *J. Cell. Biol.* 107: 481-495), mitochondria in S. pombe are organized into tubular structures (Chiron et al., (2007) *Methods Mol. Biol.* 372: 91-105), as shown in FIG. 5A. These structures are largely contiguous in appearance, typically spanning the length of the cell from tip-to-tip, and aligned with microtubules, at least to some extent, during interphase of the cell cycle (Kanbe et al., (1989) *J. Cell Sci.* 94: 647-656; Yaffe et al., (1996) *Proc. Natl. Acad. Sci. U.S.A.* 93: 11664-11668). Since rotenone has been shown to cause fragmentation of mitochondrial localization in mammalian cells, it was determined whether rotenone has a similar effect on mitochondrial localization in S. pombe. Wild type S. pombe cells were cultured to mid-log phase in YES liquid medium were treated with rotenone (6.4 µg/ml) for 4 hr, stained with the fluorescent mitochondrial dye MitoTracker Green FM (MTGreen), and visualized by fluorescence microscopy. In contrast to cells in control cultures, which exhibited a typical pattern of largely contiguous tubular mitochondrial structures (FIG. 5A), in cultures treated with rotenone, greater than 90% of cells exhibited complete or nearly complete fragmentation of mitochondrial localization (FIG. 5B). This fragmented pattern of mitochondrial localization persisted, to some extent, with continued culturing of cells in rotenone containing medium for a period of at least 24 hrs after initial exposure to the toxin (data not shown). These results demonstrate that, similar to effects documented in mammalian cells, rotenone induces disruption of mitochondrial localization in S. pombe cells.

To determine whether rotenone induces abnormalities in S. pombe cell morphology, rotenone-treated and untreated S. pombe cells were compared by DIC microscopy. Periodic examination of cells treated with rotenone for 4 to 24 hrs revealed no obvious differences in the morphological characteristics of rotenone treated (FIG. 5D) and untreated cells (FIG. 5C). Rotenone, at a concentration of 6.4 µg/ml, does not induce obvious defects in S. pombe cell morphology.

Example 6

Rotenone induces generation of ROS in S. pombe cells. Since rotenone induces generation of ROS in mammalian cell cultures and oxidative stress damage in the brains of rats chronically treated with the toxin (Li et al., (2003) *J. Biol. Chem.* 278: 8516-8525; Greenamyre et al., (2003) *Parkinsonism Relat. Disord.* 9 (Suppl 2): S59-64), it was determined whether rotenone also induces generation of ROS in *S. pombe* cells. To do this, wild type *S. pombe* cells were treated with rotenone and periodically analyzed the treated cells by staining with dihydroethidium (DHE), which is oxidized to ethidium in the presence of ROS (Bindokas et al., (1996) *J. Neurosci.* 16: 1324-1336).

Figure 7:
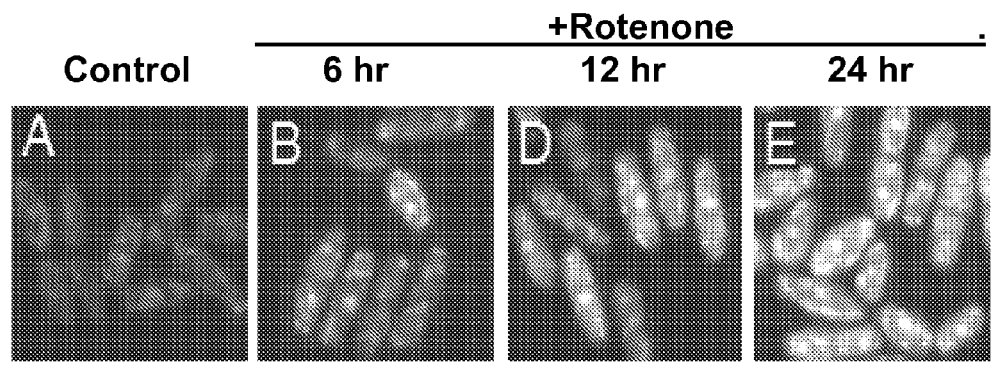
FIG. 7 shows a series of digital images illustrating that rotenone induces generation of ROS in *S. pombe* cells. *S. pombe* cells cultured to midlog phase in YES liquid medium were treated with rotenone (6.4 μg/ml) for 6, 12, or 24 hr. Control (Panel A) and rotenone-treated cells (Panels B-E) were stained with DHE and visualized by fluorescence microscopy. Control cells were treated with a volume of DMSO equivalent to that used for the rotenone treated cells (Materials and Methods).

*S. pombe* cells treated with rotenone for 6 hrs (FIG. 7, Panel B) were found to have higher levels of ROS than control cells (FIG. 7, Panel A). Higher levels of ROS were detected after 12 hr of rotenone treatment (FIG. 9, Panel C) and even higher levels after 24 hrs of exposure to the toxin (FIG. 7, Panel D). These results showed that rotenone induces production of ROS in *S. pombe*, an organism that naturally lacks complex I of the mitochondrial electron transport chain.

Example 7

The MAPK Pmk1 is required for rotenone resistance in *S. pombe*. Given the above finding that rotenone induces production of ROS in *S. pombe* cells, it was determined whether stress responsive MAPKs are required for rotenone resistance in this organism. Two MAPKs, Spc1 (alternatively known as Sty1 and Phh1) (Millar & Wilkinson (1995) *Genes Dev.* 9: 2117-2130; Kato et al., (1996) *FEBS Lett.* 378: 207-212; Shiozaki & Russell (1995) *Nature* 378: 739-743) and Pmk1 (alternatively known as Spm1) (Zaitsevskaya-Carter & Cooper (1997) *Embo J.* 16: 1318-1331; Toda et al., (1996) *Mol. Cell Biol.* 16: 6752-6764), contribute differentially to oxidative stress responses in *S. pombe*. Thus, *S. pombe* spc1Δ mutants are hypersensitive hydrogen peroxide (HP)-induced oxidative stress but are not hypersensitive to the organic oxidant t-butyl hydroperoxide (TBHP) (Degols et al., (1996) *Mol. Cell. Biol.* 16: 2870-2877; Chen et al., (2008) *Mol. Biol. Cell* 19: 308-317). Conversely, pmk1Δ cells are hypersensitive to TBHP, but not HP (Chen et al., (2008) *Mol. Biol. Cell* 19: 308-317). In addition, both Spc1 and Pmk1 are required for normal *S. pombe* cell growth in nutrient-limited conditions (Zaitsevskaya-Carter & Cooper (1997) *Embo J.* 16: 1318-1331; Shiozaki & Russell (1995) *Nature* 378: 739-743).

Figure 8A:
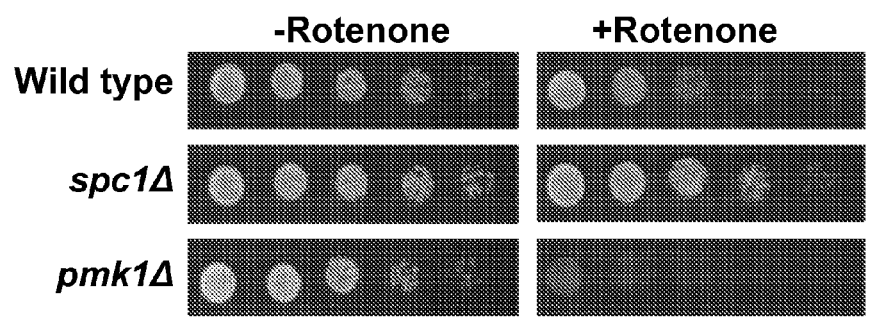
FIGS. 8A and 8B are digital images illustrating the effects of rotenone on growth of *S. pombe* MAPK mutants. Wild type, spc1Δ, and pmk1Δ cells were cultured in YES medium to mid-log phase, harvested by centrifugation, and resuspended in YES at $5 \times 10^6$ cells/ml. The cell suspensions were serially diluted (1:5) and 3 μl of each dilution was spotted onto YES or YES supplemented with rotenone (6.4 μg/ml) and the plates were incubated at 30° C. for 2 days (FIG. 8A) or 3 days (FIG. 8B) prior to scanning the plates.
Figure 8B:
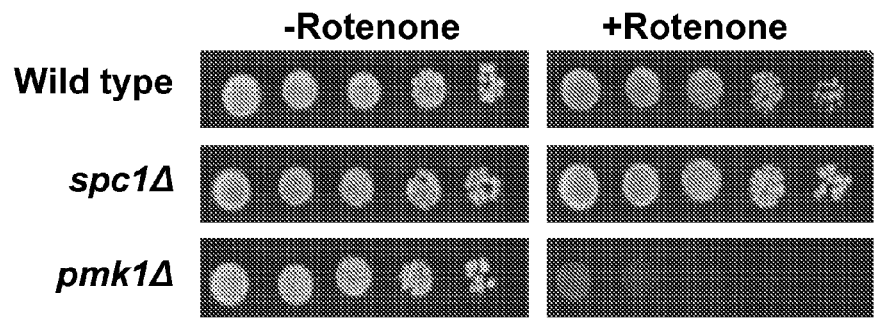

To determine whether spc1Δ and/or pmk1Δ mutants are hypersensitive to rotenone, log phase cultures of the two strains and wild type *S. pombe* cells were serially diluted and tested for growth on YES medium containing rotenone and on control medium lacking the toxin. Interestingly, we found the spc1Δ mutant was slightly less sensitive to rotenone than wild type *S. pombe* cells (FIGS. 8A and 8B). The reduced sensitivity of spc1Δ cells to rotenone was most evident after incubation of the cultures for two days (FIG. 8A), with the difference after 3 days of growth being apparent from examination of colony sizes at the end of the cell dilution series on the respective plates (FIG. 8B). In contrast to the spc1Δ mutant, the pmk1Δ mutant was profoundly more sensitive to rotenone than wild type *S. pombe* cells (FIG. 8B). These results demonstrate that Pmk1, but not Spc1, is required for normal rotenone resistance in *S. pombe*.

Example 8

Pmk1, but not Spc1, is required for normal clearance of rotenone-induced ROS in *S. pombe* cells. To investigate further the effects of rotenone on spc1Δ and pmk1Δ cells, we treated the two strains and wild type *S. pombe* cells were treated with rotenone for 12 hrs and stained cells from treated and control cultures with DHE for detection of ROS by fluorescence microscopy.

ROS levels were similar in control cultures of wild type (FIG. 9A) and pmk1Δ cells (FIG. 9C) and, by comparison, slightly reduced in spc1Δ cells (FIG. 9B). Consistent with results of growth assays described above, we found that, in contrast to wild type cells (FIG. 9D), rotenone induced only a very slight increase in ROS levels in spc1Δ cells (FIG. 9E). In contrast, rotenone induced levels of ROS production in pmk1Δ cells that were dramatically higher than those induced in wild type cells (FIG. 9F).

These findings indicate that physiological clearance of rotenone-induced ROS in *S. pombe* is at least partially dependent on the MAPK Pmk1 but not on the MAPK Spc1. Indeed, spc1Δ cells accumulate proportionately less ROS in response to rotenone exposure than wild type *S. pombe* cells, suggesting that they are physiologically sensitized to the toxin.

Example 10

Figures 10A, 10C:
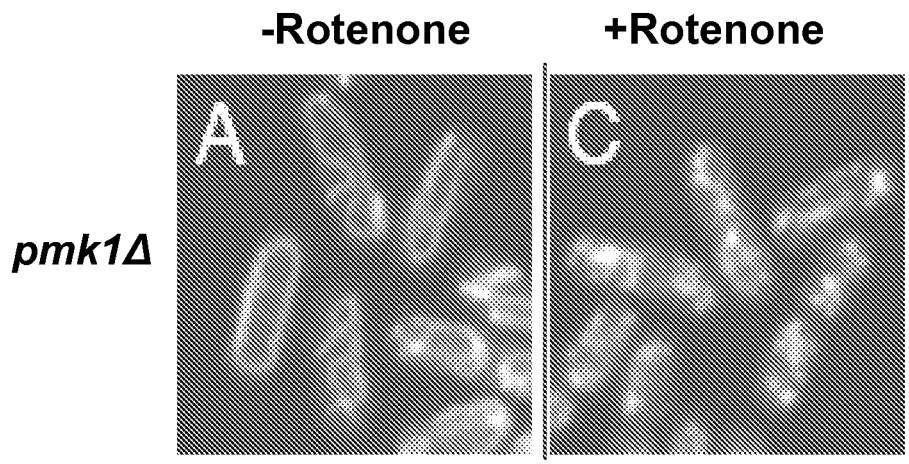
FIGS. 10A-10D shows a series of digital images illustrating the effects of rotenone on mitochondrial localization in *S. pombe* MAPK mutants. Fluorescence photomicrographs of pmk1Δ and spc1Δ cells stained with MTGreen for visualization of mitochondrial localization.
Figures 10B, 10D:
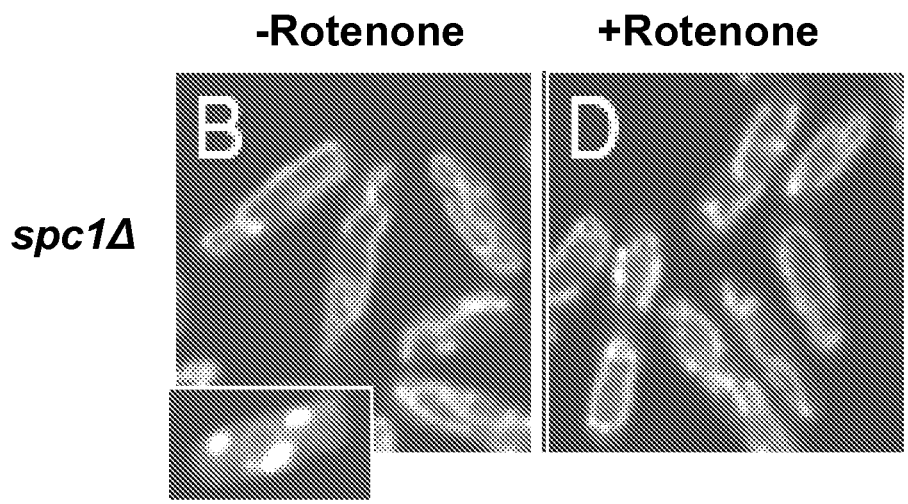

Effects of rotenone on mitochondrial localization in pmk1Δ and spc1Δ cells. The effects of rotenone on mitochondrial localization in pmk1Δ and spc1Δ cells were examined. In untreated pmk1Δ cells, similar to wild type cells (shown in FIG. 5A), mitochondria were organized into largely contiguous tubular structures (shown in FIG. 10A), suggesting that under normal culturing conditions, Pmk1 is not required for maintenance of mitochondrial organization in *S. pombe*. Mitochondria were also organized into tubular structures in spc1Δ cells (FIG. 10B), although in a small percentage of cells in spc1Δ cultures, mitochondria were found to be concentrated into cytoplasmic aggregates, in most cases without detectable tubular mitochondrial localization (FIG. 10B, inset panel).

Rotenone induced marked fragmentation of mitochondrial localization in pmk1Δ cells (FIG. 10C), although at a lower frequency (approximately 70% of cells) than that detected in cultures of wild type *S. pombe* cells (>90% of cells). In contrast, rotenone had a marginal effect on mitochondrial localization in spc1Δ cells, the majority of which retained tubular mitochondrial structures after rotenone treatment (FIG. 10D). These results demonstrate that spc1Δ cells exhibit marked resistance to rotenone-triggered cellular perturbations that in wild type and pmk1Δ cells lead to fragmentation of mitochondrial localization at relatively high frequencies.

We claim:

1. A method of identifying a test compound characterized by reducing rotenone inhibition of proliferation of a strain of a yeast *Schizosaccharomyces pombe*, comprising:
    (a) obtaining a culture of a strain of the yeast, wherein the proliferation of the yeast when in contact with rotenone is reduced compared to the proliferation of the yeast when not in contact with rotenone;
    (b) contacting the yeast in contact with rotenone with a test compound; and
    (c) determining whether the proliferation of the yeast in contact with rotenone and with the test compound increases compared to the proliferation of the yeast in contact with rotenone but not
    with the test compound, thereby indicating whether the test compound reduces inhibition of yeast proliferation by rotenone, wherein the *Schizosaccharomyces pombe* is maintained under culture conditions comprising a limited nutrient minimal medium and/or comprises a mutation of at least one gene, said mutation conferring sensitivity of the yeast to proliferative inhibition by rotenone, wherein the at least one gene is aks1, pmk1, or psd1, psd2 and psd3.

2. The method of claim 1, wherein the step of contacting the yeast in contact with rotenone with the test compound comprises delivering to the yeast at least one test heterologous nucleic acid, and wherein the method further comprises the steps:
   (i) isolating the yeast receiving the at least one test heterologous nucleic acid and having increased proliferation in the presence of rotenone as compared to the proliferation of an untransformed yeast in contact with rotenone; and
   (ii) identifying the at least one heterologous nucleic acid, wherein said heterologous nucleic acid confers resistance to rotenone on the unicellular fungus yeast.

3. The method of claim 1, wherein the culture medium is rich complete medium and the yeast comprises the mutation of the at least one gene.

4. The method of claim 1, wherein the at least one gene is aks1 or pmk1.

5. The method of claim 1, wherein the at least one gene is psd1, psd2 and psd3.

6. The method of claim 1, wherein the *Schizosaccharomyces pombe* is maintained under culture conditions comprising a limited nutrient minimal medium.

* * * * *